(12) United States Patent
Gueret (10) Patent No.: US 6,419,935 B1
(45) Date of Patent: Jul. 16, 2002

(54) COSMETIC SKIN TREATMENT METHOD AND CLEANSING TREATMENT PATCH

(75) Inventor: Jean-Louis H. Gueret, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/363,171

(22) Filed: Jul. 29, 1999

(30) Foreign Application Priority Data

| Jul. 30, 1998 | (FR) | 98 09794 |
| Jul. 30, 1998 | (FR) | 98 09795 |
| Jul. 31, 1998 | (FR) | 98 09880 |

(51) Int. Cl.$^7$ ............................. A61K 7/00; A61K 7/48
(52) U.S. Cl. ................... 424/401; 424/78.03; 424/448; 128/268
(58) Field of Search ............................. 424/401, 78.03, 424/448; 128/268

(56) References Cited

U.S. PATENT DOCUMENTS

| 3,428,043 A | | 2/1969 | Shepherd |
| 3,499,446 A | | 3/1970 | Tsuneizumi et al. |
| 3,996,934 A | * | 12/1976 | Zaffaroni ..................... 128/268 |
| 4,377,160 A | | 3/1983 | Romaine |
| 4,585,797 A | | 4/1986 | Cioca |
| 4,631,227 A | | 12/1986 | Nakamura |

(List continued on next page.)

FOREIGN PATENT DOCUMENTS

| AT | AS 206 114 | 11/1989 |
| DE | 44 46 380 | 1/1996 |
| EP | 0 063 875 | 11/1982 |
| EP | 0 190 814 | 8/1986 |
| EP | 0 309 309 | 3/1989 |
| EP | 0 412 869 | 2/1991 |

(List continued on next page.)

OTHER PUBLICATIONS

English language Derwent Abstract of DE 44 46 380, Dec. 23, 1994.
English language Derwent Abstract of EP 0 764 441, Sep. 19, 1996.
English language Derwent Abstract of FR 2 276 030, 1976.
English language translation of FR 2 515 651, Mar. 18, 1983.
English language translation of FR 2 538 247, Jun. 29, 1984.
English language Derwent Abstract of FR 2 738 744, Mar. 21, 1997.

Primary Examiner—Jose' G. Dees
Assistant Examiner—Mina Haghighatian
(74) Attorney, Agent, or Firm—Finnegan, Henderson, Farabow, Garrett & Dunner, L.L.P.

(57) ABSTRACT

A cosmetic skin treatment method includes providing a patch configured to be used in both a cleansing mode and a treatment mode. The patch includes a polymeric matrix and a reinforcing member. The polymeric matrix includes at least one cosmetically active compound and at least one water-absorbent compound. The patch is configured to adhere to dry skin and also to adhere to skin when at least one of the patch and skin are moistened. The method also includes selecting at least one of the cleansing mode and the treatment mode. When the cleansing mode is selected, the method further includes applying the patch to an areas of dry skin so that the polymeric matrix adheres to the skin for a time sufficient to allow at least one impurity in the area of skin to become attached to the polymeric matrix. Thereafter, the patch is removed from the area of the skin while said at least one impurity is attached to the polymeric matrix. When the treatment mode is selected, the method further includes moistening at least one of the patch and an area of the skin. Then, the patch is applied to the area of skin so that the patch adheres to the area of skin. After applying the patch, the cosmetically active compound is allowed to contact the area of skin. A cleansing and treatment patch is also disclosed.

81 Claims, 1 Drawing Sheet

U.S. PATENT DOCUMENTS

| | | | |
|---|---|---|---|
| 4,643,939 A | | 2/1987 | Sugiyama et al. |
| 4,814,167 A | | 3/1989 | Wirth et al. |
| 5,026,552 A | | 6/1991 | Gueret et al. |
| 5,100,672 A | | 3/1992 | Gueret et al. |
| 5,232,707 A | | 8/1993 | Lokensgard |
| 5,374,429 A | | 12/1994 | Kinoshita et al. |
| 5,449,519 A | * | 9/1995 | Wolf et al. ............ 424/401 |
| 5,466,456 A | | 11/1995 | Glover |
| 5,466,724 A | | 11/1995 | Volke et al. |
| 5,512,277 A | * | 4/1996 | Uemura et al. ........ 424/78.03 |
| 5,536,263 A | * | 7/1996 | Rolf et al. ............ 604/307 |
| 5,811,107 A | | 9/1998 | Gangadharan et al. |
| 5,935,596 A | * | 8/1999 | Crotty et al. ............ 424/448 |

FOREIGN PATENT DOCUMENTS

| | | |
|---|---|---|
| EP | 0 651 984 | 5/1995 |
| EP | 0 764 441 | 3/1997 |
| FR | 2 276 030 | 1/1976 |
| FR | 2 515 651 | 3/1983 |
| FR | 2 538 247 | 6/1984 |
| FR | 2 738 744 | 3/1997 |
| FR | 2 750 050 | 12/1997 |
| GB | 2 265 086 | 9/1993 |
| WO | WO 87/05206 | 9/1987 |
| WO | WO 94/02674 | 2/1994 |
| WO | WO 94/17837 | 8/1994 |
| WO | WO 94/22423 | 10/1994 |
| WO | WO 95/05204 | 2/1995 |
| WO | WO 95/28136 | 10/1995 |
| WO | WO 96/14822 | 5/1996 |
| WO | WO 98/31315 | 7/1998 |
| WO | WO 98/42303 | 10/1998 |

OTHER PUBLICATIONS

English language Derwent Abstract of FR 2 750 050, Aug. 1998.

English language translation of AS 206 114.

* cited by examiner

COSMETIC SKIN TREATMENT METHOD AND CLEANSING TREATMENT PATCH

The present application refers to U.S. patent application Ser. No. 09/362,680, filed on Jul. 29, 1999 and U.S. patent application Ser. No. 09/362,681, filed on Jul. 29, 1999. The disclosure of both of these applications is incorporated herein by reference.

The present invention relates to a cosmetic skin treatment method using a patch configured to be applied to the skin in a cleansing mode to cleanse the skin and in a treatment mode to provide one or more treatments to the skin. The invention also relates to a cleansing and treatment patch that can be used to practice the method.

Conventional methods employ patches that allow active compounds to be administered transdermally for the purpose of carrying out a systemic treatment. Such conventional patches generally have a structure that includes several successive layers. The first layer is a support layer. The support layer is generally occlusive. The second layer is a composition that is fastened to the support layer and often contains one or more active compounds. The composition layer is the layer that contacts the skin during treatment. The composition layer may also include an adhesive to facilitate fastening of the patch to the skin. The last layer is a detachable cover. The cover generally sealably covers the composition layer to protect it from external contamination during storage of the patch prior to use.

Occlusive beauty care patches are also known in the art. Those patches are configured to allow active compounds to penetrate the epidermis. They generally do not include an adhesive since they often include aqueous or hydrophilic formulations. Occlusive beauty patches are intended for skin treatment and are generally placed on the skin for an application time that may range from 15 minutes to 8 hours.

Some occlusive beauty care patches are applied overnight for administering an active agent to the epidermis. Those patches often exhibit a very high level of adhesion to the skin and therefore can damage the skin when they are removed. In particular, patches with strong adhesives can cause cracking, painful red blotches, and/or inflamation to skin that has already become sensitive due to prior treatments.

Dry masks are also known. Dry masks require the user to moisten the mask prior to applying the mask. Dry masks are generally intended for deep cleansing of the skin, especially of the pores. However, dry masks tend to dry out the skin.

Dehydrated patches that can be remoistened with water are also known. Those patches include water-soluble polymers. Dehydrated patches are removed after drying to desquamate and cleanse the skin.

Additionally, self-adhesive patches that comprise a hydrophobic matrix made of polyurethane, polyacrylate, polyvinyl, or silicone are known. Those patches include water-absorbing particles. The water absorbing particles re-dissolve water-soluble active agents contained in the matrix, forming a suspension. Patches of this kind, however, exhibit a relatively limited level of adhesion.

Dry non-bonding treatment-cloth products that are moistened and do not dry out are also known. They are generally used to carry out facial beauty care treatments.

In light of the foregoing, there is a need in the art for an improved cosmetic skin treatment method and an improved cleansing and/or treatment patch.

Accordingly, the present invention is directed to a cosmetic skin treatment method and a cleansing and/or treatment patch that obviate one or more of the short-comings of the related art.

A preferred object of the invention is to provide a treatment method that allows a user to apply a single patch to cleanse the skin and to allow treatment of the skin.

Another preferred object of the invention is to provide a dual purpose patch that can be used in a cleansing mode and a treatment mode. Having a dual purpose patch obviates the risk of confusing different types of patches.

Preferably, in addition to cleansing the skin, the patch of the present invention can be used to provide a treatment. In particular, the patch can provide a treatment in which one or more cosmetically active compounds are released onto the epidermis.

Using the patch in the cleansing mode preferably prepares the skin for treatment by removing impurities present on the surface of the skin. For example, such impurities include residues due to environmental pollution, dead skin cells, sebum plugs, blackheads, and perspiration residues.

After the patch is used to cleanse the skin, another patch of the same type, or even the same patch, can be applied to the surface of the skin to provide a treatment. For example, the treatment may include an emolliating, moisturizing, softening, cicatrizing, regenerating, anti-wrinkling or tautening, sun-screening, soothing, self-tanning, or lightening action on the skin. The treatment may also include opening or closing pores of the skin.

A further preferred object is to provide a simple, alternating and/or cumulative skin cleansing and skin treatment using the same type of patch.

Still another object of the invention is to provide two different treatments depending on whether the patch is applied to dry skin when the patch is in a dried state or to skin when the patch is in a wet state (i.e., at least one of the patch and the skin is moistened).

Another object of the invention is to provide a patch incorporating various cosmetically active compounds which, apart from removing impurities from the skin, provide a treatment to the skin, such as a moisturizing, softening, emolliating, cicatrizing, regenerating, soothing, self-tanning, lightening, anti-wrinkling, sun-screening action, or grease-reducing treatment.

An additional object of the invention is to prepare the skin for a skin treatment by cleansing the skin, thereby increasing the effectiveness of the skin treatment.

It should be understood that the invention could still be practiced without performing one or more of the preferred objects and/or advantages set forth above. Still other objects will become apparent after reading the following description of the invention.

To achieve these and other advantages, and in accordance with the purposes of the invention, as embodied and broadly described herein, the invention includes a cosmetic skin treatment method. The method includes providing a patch configured to be used in both a cleansing mode and a treatment mode. The patch includes a polymeric matrix and a reinforcing member. The polymeric matrix includes at least one to cosmetically active compound and at least one water-absorbent compound. The patch is configured to adhere to dry skin and also to adhere to skin when at least one of the patch and skin is moistened. Preferably, an adhesion force between the patch and dry skin is greater than an adhesion force between the patch and skin when at least one of the patch and skin is moistened. The method also includes selecting at least one of the cleansing mode and the treatment mode. When the cleansing mode is selected, the method further includes applying the patch to an area of dry skin so that the polymeric matrix adheres to the skin for a time sufficient to allow at least one impurity in the area of skin to become attached to the polymeric matrix. Thereafter, the patch is removed from the area of the skin while said at least one impurity is attached to the polymeric matrix. When the treatment mode is selected, the method further includes moistening at least one of the patch and an area of the skin. Then, the patch is applied to the area of skin so that the patch adheres to the area of skin. After applying the patch, the cosmetically active compound is allowed to contact the area of skin. The cosmetically active compound is preferably allowed to dissolve in the moisture. Preferably, the patch is removed from the area of skin.

Although in the treatment mode either the patch or the skin can be moistened, moistening of the skin is the preferred method.

The patch preferably includes a self-adhesive matrix allowing the patch to adhere to dry skin. Preferably, at least a substantial portion of the area of the patch contacts the skin. When the patch is removed, impurities on the surface of the skin are preferably removed due to the mechanical action of the adhesive. Preferably, the polymeric matrix includes active agents that facilitate removal of the impurities. For example, active agents may be transferred to the skin when the patch is removed from the skin.

The at least one water absorbent compound is preferably separated from the free surface of the patch by a very thin layer of adhesive material. When moisture is applied to the patch by moistening the patch or by contacting the patch with moistened skin, the at least one water absorbent compound preferably absorbs moisture and forms a gel or a network of water-swollen fibers, into which the at least active compound is dissolved. When the at least one active compound is dissolved in the gel of water-swollen fibers, it can be brought into contact with the skin. Because the at least one water absorbent compound absorbs some of the moisture, a certain number of anchoring points preferably remain between the matrix and the skin, thereby allowing sufficient adhesion of the patch to the skin. When moisture is applied to the patch, the adhesion force between the patch and the skin is preferably substantially less than the adhesion force between the patch and dry skin.

In a preferred embodiment, the method includes selecting both the cleansing mode and the treatment mode, wherein the cleansing mode is performed prior to the treatment mode. Although the treatment may be performed immediately after the cleansing, the cleansed skin is preferably allowed to rest after the cleansing, for example, the cleansed skin is allowed to rest for a period ranging from about 30 minutes to about 12 hours.

In another embodiment, the method includes selecting both the cleansing mode and the treatment mode, wherein the treatment mode is performed prior to the cleansing mode. For example, an emolliating treatment is applied prior to cleansing to open the pores to facilitate a subsequent deep cleansing.

Preferably, the application of the patch in cleansing mode is carried out alternately with the application in treatment mode. However, it may be advantageous, especially when the skin is greasy, to carry out a number of applications in cleansing mode alternating with a number of applications in treatment mode.

Preferably, when using the patch in the cleansing mode, the patch is applied for a period ranging from about 5 seconds to about 5 minutes.

When the patch is used in the treatment mode, the application may be carried out for a period ranging from about 5 minutes to about 30 minutes, or even about 60 minutes, if required.

In another aspect, the invention includes a cleansing and treatment patch. The patch includes a reinforcing member and a polymeric matrix. The polymeric matrix includes at least one cosmetically active compound and at least one water-absorbent compound. The patch is configured to adhere to dry skin and also to adhere to skin when at least one of the patch and skin are moistened. Preferably, an adhesion force between the patch and dry skin is greater than an adhesion force between the patch and skin when at least one of the patch and skin are moistened. The patch is configured so that when the patch is used in a cleansing mode and the patch is applied to an area of dry skin, the patch adheres to the area for a sufficient time to allow at least one impurity in the area of skin to become attached to the polymeric matrix so that the impurity is removed from the area of skin when the patch is removed. The patch is also configured so that when the patch is used in a treatment mode and at least one of the patch and an area of skin is moistened, at least some of the cosmetically active compound contacts the area of skin. When the patch is used in treatment mode, preferably at least some of the cosmetically active compound is dissolved in the moisture.

The cosmetically active compounds that can be incorporated into the matrix of the patch are preferably chosen from emollients, moisturizers, softening agents, keratolytic agents, desquamating agents, cicatrizing agents, regenerating agents, anti-wrinkle agents, tautening agents, sun-screen agents, soothing agents, self-tanning agents, bleaching agents, lightening agents or mixtures thereof. In addition, antioxidants, free-radical scavengers, liporegulating agents, anti-acne agents, anti-ageing agents, anti-inflammatory agents, refreshing agents, vascular protective agents, antibacterials, antifungals and nourishing agents may be incorporated into the polymeric matrix.

In a preferred embodiment, the at least one cosmetically active compound is dispersed homogeneously in the polymeric matrix in particulate form. Homogeneous dispersion of the at least one cosmetically active compound can be beneficial, especially when the patch is applied in treatment mode to wet skin, since the at least one cosmetically active compound dissolves substantially in the matrix, resulting in even penetration.

The at least one cosmetically active compound is used especially in the cleansing mode. It is preferably a compound whose action allows the impurities in the skin to become detached from the skin (for example, keratolytic agents that detach dead skin cells). There may also be one or more compounds contained in the matrix that are capable of directly absorbing the fatty or aqueous secretions of the skin, such as sebum or perspiration. For this purpose, it is possible to use materials such as kaolin powder, burnt Sienna, zeolites, polyamide particles (especially those sold under the name ORGASOL® by the company Atochem). These particles also may have a softening effect on the skin. Powder of expanded thermoplastic microspheres, sold under the brand name EXPANCEL® by the company Kemanord Plast, and modified starch powders sold by the company National Starch under the brand name Dry Flo® may also be used to absorb fatty or aqueous secretions. It is further possible to use a mixture of such materials.

The active compounds having a cleansing effect that may be incorporated into the matrix include, in particular, keratolytic agents such as alpha- and beta-hydroxycarboxylic acids and beta-ketocarboxylic acids, their salts, amides and esters, and preferably alpha-hydroxy acids such as glycolic acid, lactic acid, tartaric acid, malic acid, citric acid, mandelic acid and, in general, fruit acids and beta-hydroxy acids such as salicylic acid and its derivatives, especially alkylated derivatives such as 5-(n-octanoyl)salicylic acid and its esters. Antibacterials such as clindamicyn or erythromycin phosphate, or antibiotics of the tetracyclin type may also be used. Such active compounds are preferred when the skin has a tendency towards acne and can be used in particular in combination with emollients, softening agents, especially honey and waxes and/or cicatrizing agents, especially certain mineral salts, such as zinc oxide. They may also be combined with astringent agents such as tannins and/or aluminium and/or zirconium chlorohydrates.

The at least one active compound may include one or more active agents chosen from ascorbic acid and its biologically compatible salts and esters, enzymes, tautening agents, such as protein, soya and wheat powders, hydroxylated polyacids, sucroses and their derivatives, urea, amino acids, oligopeptides, water-soluble plant and yeast extracts, protein hydrolysates such as collagen and elastin hydrolysates, hyaluronic acid, mucopolysaccharides, vitamins $B_2$, $B_6$, H and PP, panthenol, folic acid, acetylsalicylic acid, allantoin, kojic acid, and hydroquinone.

The matrix may also include at least one liposoluble compound chosen from the following compounds: D-α-tocopherol, DL-α-tocopherol, D-α-tocopherol acetate, DL-α-tocopherol acetate, ascorbyl palmitate, vitamin F and vitamin F glycerides, vitamins D, vitamin $D_2$, vitamin $D_3$, retinol, retinol esters, retinol palmitate, retinol propionate, β-carotene, D-panthenol, farnesol, farnesyl acetate; jojoba and blackcurrant oils rich in essential fatty acids; asiatic acid, madecassic acid, asiaticoside, total extract of centella asiatica, β-glycyrrhetinic acid, α-bisabolol, ceramides such as 2-oleoylamino-1,3-octadecane; phytanetriol, milk sphingomyelin, phospholipids of marine origin, rich in polyunsaturated essential fatty acids, ethoxyquin; extract of rosemary, extract of melissa, quercetin, extract of dried microalgae, and steroidal anti-inflammatory drugs.

By way of example, the emollient can be chosen from: volatile and non-volatile silicones, polydiorganosiloxane-polyoxyalkylene copolymers; natural and synthetic oils such as mineral, plant and animal oils; fats and waxes; fatty alcohols and acids, and their esters; esters and ethers of (poly)alkylene glycols; hydrocarbons such as isohexadecane, petrolatum and squalane; lanolin alcohol and its derivatives; animal and plant triglycerides; and stearyl alcohol.

The moisturizer is preferably chosen from: glycerol, sorbitol and its derivatives, propylene glycol, dipropylene glycol, butylene glycol, D- or DL-panthenol and their derivatives.

Preferably, allantoin is chosen as a softening agent.

The desquamating agent is chosen from: alkylated derivatives of salicylic acid, 5-(n-octanoyl)salicylic acid, alpha- and beta-hydroxycarboxylic acids and beta-ketocarboxylic acids, their salts, amides and esters.

The tautening agents are preferably chosen from alpha- and beta-hydroxycarboxylic acids and beta-ketocarboxylic acids, their salts, amides and esters; alicyclic acid, ascorbic acid, azelaic acid, retinol and their derivatives.

When sunscreen agents are present, they are preferably chosen from the UV-A filters and/or the UV-B filters normally used in sunscreen compositions.

As a soothing agent, α-bisabolol can be chosen.

When a self-tanning agent is used, it is chosen from dihydroxyacetone and derivatives of hydroxynaphthoquinone.

Preferably, the lightening or bleaching agent is chosen from citric acid, hydroquinone, kojic acid and ascorbic acid.

Preferably, the polymeric matrix includes a silicone adhesive. More preferably, the polymeric matrix includes a polyacrylic or polyvinyl adhesive, such as a self adhesive acrylic polymer sold by the company MAPEI, S.p.A. under the brand name AGXL®.

The adhesion force of the patch to dry skin (when used in cleansing mode) preferably ranges from about 300 g/cm² to about 800 g/cm² (i.e., a force exerted perpendicular to the plane of the adhesive surface needed to pull the patch off of the skin). The adhesion force of the patch when moistened preferably ranges from about 20 g/cm² to about 300 g/cm².

The surface of the matrix that contacts skin may be smooth or may have asperities or raised features. The thickness of the matrix may vary, depending on the amount of the at least one active compound and the at least one water-absorbent compound used. Preferably, the thickness ranges from about 5 microns to about 500 microns.

In an aspect of the invention, when the matrix initially includes one or more solvents, after the solvents have evaporated, at least some of the particles of the at least one active compound and/or at least some of the particles of the water-absorbent compounds and/or agglomerates formed from such particles, emerge from an application surface of the adhesive matrix. In practice, these particles generally do not emerge directly, but remain coated with a very thin layer of the matrix. By way of example, the particles have a thickness that ranges from a few microns to a few hundred microns. Preferably, the thickness of the particles ranges from about 10 microns to about 100 microns, and even more preferably from 10 microns to about 70 microns. Preferably, the average thickness of the matrix (after evaporation of the solvents) is less than the largest dimension of fillers and/or particles of the at least one active compound and/or particles of the at least one water-absorbent compound present in the matrix. Where appropriate, if the fillers or particles form agglomerates, (i.e., groups) the average thickness of the matrix is preferably less than the largest dimension of said agglomerates. This arrangement allows the formation of an interface layer when moisture is applied to the patch for the treatment mode. The interface layer is preferably formed by at least one water absorbent compound swollen with moisture (i.e., water), especially in the form of a gel. Preferably, the active compounds are capable of dissolving in the interface layer. The interface layer is preferably between the matrix and the skin, thereby allowing the at least one active compound to be brought into contact with the skin. The thickness of the interface layer preferably ranges from about 50 microns to about 100 microns. Although only a small portion of the adhesive matrix is in contact with the skin, resulting in a reduced adhesion to the skin, the adhesive matrix generates sufficient adhesion force to maintain the patch on the skin due at least in part to the intrinsic adhesion of the gel.

Preferably, the at least one water-absorbent compound comprises particles dispersed in the matrix. When the particles of the at least one water-absorbent compound contact moisture present on the skin (e.g., after moistening the skin), the particles of the water-absorbent compound absorb moisture, thereby facilitating dissolving of a water-soluble solid active compound when a water soluble solid active compound is present in the matrix. This in situ solubilization of the water-soluble active compound provides for almost instantaneous bioavailability. Additionally, interaction with other compounds present in the polymeric matrix is minimized. The moisture present on the skin (or on the patch before application) acts as a solublizer for a water-soluble active compound.

Representative water-absorbent compounds that may be present in the polymeric matrix in the dispersed state include superabsorbent crosslinked polyacrylates having a high degree of swelling in water, such as those sold by the company Norsolor under the brand name AQUAKEEP®; polyvinyl alcohol; carboxyvinyl polymers such as those sold by Goodrich under the brand names CARBOPOL®; semi-synthetic derivatives of cellulose such as carboxymethylcellulose; starches, biogums such as xanthan gum, guar gum, gum arabic and gum tragacanth, biosaccharides, scleroglucans; casein; phytocolloids, such as alginates, carragenates and agar agar; gelatin and cotton fibers.

It is particularly preferable to use superabsorbent crosslinked polyacrylates, whose presence in the dispersed state in a hydrophobic polymeric matrix allows a high water content to be built up and favors, after hydration, better availability of the particles of other active compounds possibly present in the matrix.

The at least one water-absorbent compound defined above is preferably present in an amount ranging from about 0.2% to about 20% with respect to the total weight of the matrix, and even more preferably ranging from about 0.5% to about 10% with respect to the total weight of the matrix.

Essential oils may be included in the polymeric matrix. By way of example, mention may be made of lavender, mint, pepper, nutmeg, clove, cedar, wheatgerm, calophyllum, cartham, coriander and fruit pip (grape, blackcurrant, orange and kiwi) oils. Mint oil contains a high level of menthol which, when included in the matrix in microcrystalline form, can provide skin with a feeling of freshness.

The reinforcing member preferably includes any suitable material impermeable to the active compounds contained in the polymeric matrix. The reinforcing member not only has the function of reinforcing the polymeric matrix, but also serves as a coating for protecting the matrix. The reinforcing member may have the same size as the polymer matrix or it may be larger so that it extends beyond the periphery of the polymeric matrix.

In an embodiment, the reinforcing member is occlusive. By way of example, the reinforcing member includes a thermoplastic chosen from high-density and low-density polyethylenes, polypropylenes, polyvinyl chlorides, ethylene-vinyl acetate copolymers, polyesters and polyurethanes, and polyethylene terephthalate. These materials may also be present in the form of a laminate with at least one metal foil such as aluminium foil.

The reinforcing member preferably has a thickness suitable for providing support and protection functions. Preferably, the thickness of the reinforcing member ranges from about 20 µm to about 1.5 mm. Preferably, the reinforcing member is flexible enough to be able to match the profile of the skin and not to cause the user any feeling of discomfort.

In an alternate embodiment, the reinforcing member is non-occlusive. For example, the reinforcing member is chosen from paper, meshes of porous thermoplastic, meshes of perforated thermoplastic, woven fabrics, and nonwoven fabrics, such as perforated nonwoven fabrics. Preferably, when the reinforcing member is a mesh, the reinforcing member is embedded in the polymeric matrix.

The accompanying drawings are included to provide a further understanding of the invention and are incorporated in and constitute a part of this specification. The drawings illustrate examples of alternative embodiments of the invention and, together with the description, serve to explain the principles of the invention. In the drawings.

Figure 1:
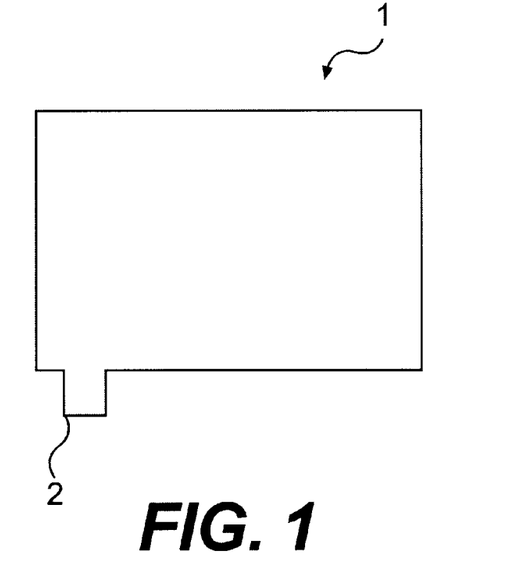
FIG. 1 shows a schematic view of a first embodiment of a patch having a portion of the patch extending therefrom.

As shown in FIG. 1, a portion 2 of a patch 1 extends from the patch 1, forming a grip to facilitate removal of the patch from the area of skin. Preferably, the portion 2 of the patch 1 is a tab. For example, the tab portion 2 could be a part of the reinforcing member of the patch 1.

Figure 2:
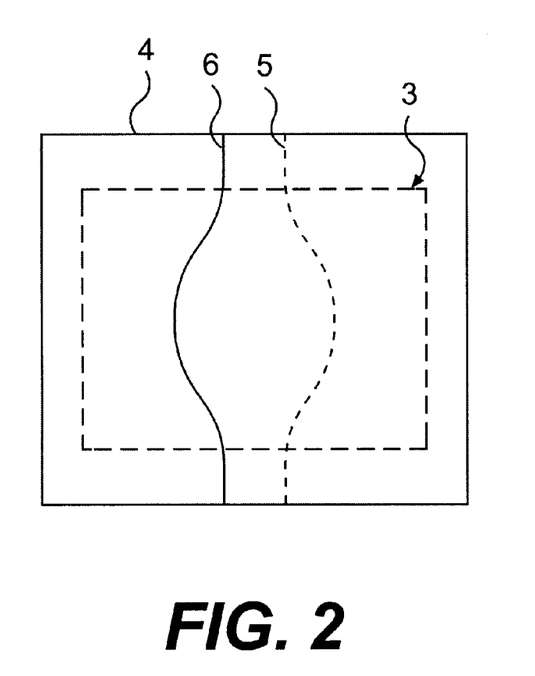
FIG. 2 shows a schematic view of a second embodiment of a patch covered by a protective film.

As shown in FIG. 2, a patch 3 preferably includes a detachable (e.g., peelable) protective film 4 configured to be peeled off of an application surface of the patch before the patch is applied. The protective film 4 includes a first part 5 and a second part 6 superposed on a central portion of the patch 3. This configuration facilitates removal of the protective film 4 while limiting a user's unintentional contacting of the matrix or the at least one active compound. The protective film is preferably adjacent to the polymeric matrix. In an alternate embodiment, the patch is protected by a package (not shown) that is impermeable to both liquid and vapor water. The protective film may have either a smooth or a corrugated surface. When the protective film has a corrugated surface, the adhesion force between the film and the matrix is reduced, thereby facilitating removal of the film.

When the polymeric matrix is protected by a detachable protective film, the film is preferably removed at the time of use. The film may be formed of any material that is impermeable to both the at least one active compound and any other compound present in the polymeric matrix. Preferably, the protective film is made of a sheet of siliconized paper or a sheet of thermoplastic treated with a non-stick treatment (e.g., treated with a silicone or a varnish). Preferably, the detachable protective film is made of polyethylene. The protective film may also extend over an area greater than the area of the patch to facilitate removal of the protective film.

In a preferred embodiment, the polymeric matrix is colored to allow a user to quantify and/or qualify the impurities removed from the skin by the adhesive surface of the patch (i.e., matrix) during the cleansing mode. The matrix preferably includes colored pigments to color the patch. For example, the patch could be constructed identical to or similar to one or more of the patches disclosed in U.S. application Ser. No. 09/240,603, filed Feb. 1, 1999, the disclosure of which is incorporated herein by reference. Preferably, the color is dark to produce sufficient contrast to allow visualization of the impurities extracted from the skin. After the patch is removed from the skin, the impurities extracted during the treatment are preferably on the colored matrix.

With knowledge of the amount of impurities removed from the skin, the user can calculate the desired frequency of cleansing with the patch. If the patch includes a large amount of impurities after removal in the cleansing mode, the user should apply the patch in the cleansing mode more often (e.g., every day). A smaller amount of impurities indicates that the frequency of cleansing may be lowered (e.g., once a week). Advantageously, when applying the patch in the cleansing mode, the coloring of the patch makes it possible to quantify the effectiveness of the treatment that is provided. Furthermore, with knowledge of the type of impurities removed from the skin, the user can select the best time period of application for the treatment mode.

The pigments preferably include pigments of the type used in the food and/or cosmetic fields, for example, pigments used for lipsticks and/or nail varnishes. By way of examples, the pigments are chosen from, alone or in combination, synthetic pigments, mineral pigments, especially zirconium oxide or cerium oxide pigments, as well as iron or chromium oxides and ferric blue. Organic pigments may also be used, especially carbon black, lacquers of barium, zirconium (D&C Red No. 9), strontium (D&C Red No. 6), calcium (D&C Red No. 7) and aluminium; azo and anthraquinone dyes (D&C Violet No. 2).

Preferably, the patches are cut to shapes designed to fit on various parts of the body. For example, the patches are cut in the shape of a mask for application to the face. Additionally, the patches are shaped to fit on the nose, lips, cheeks, the region between the nose and the upper lip, the outer corners of the eyes for treating crow's feet, under the eyes for treating bags under the eyes, and on the forehead for treating forehead wrinkles. Of course, the patches according to the present invention may be cut to any shape necessary for application to a particular area of the body. Preferably, the size of a patch ranges from 0.25 cm² to 500 cm². More preferably, the size ranges from 1 cm² to 30 cm².

After removing the detachable protective layer, the patch may be applied to an area of skin to be treated by applying it directly to the area of skin to cleanse the area of skin. During the cleansing, the at least one active compound helps to extract impurities from the skin and to remove dead cells by penetrating the epidermis and the deeper layers of the skin. Because of the strong adhesion of the patch when applied dry, the impurities and dead cells remain bonded to the exposed surface of the patch. Removal of the patch after the cleansing mode may be accompanied by a slight irritation of the skin, manifested by the appearance of a slight redness, caused by increased blood flow to the dermis. The strong adhesion allows better diffusion of the at least one active compound into the epidermis, into the deeper layers of the dermis, or even, long term, stimulation of cutaneous angiogenesis.

After removing the patch and allowing the area of skin to rest for a suitable period of time, the user preferably applies a second patch of the same type to the same area of skin, premoistened with water, to provide a treatment. Preferably, the duration of application in the treatment mode is longer than the duration of application in the cleansing mode. After allowing the patch to contact the area of skin in the treatment mode for a suitable period of application, active treatment compounds in the matrix are dissolved in the interface layer formed on the matrix and are brought into contact with the skin. The adhesion of the patch to the area of skin in the treatment mode is facilitated by the presence of the water-absorbent compounds, which preferably retain an amount of water necessary for dissolving the active treatment compounds and create anhydrous points of anchoring to the surface of the matrix, thereby allowing the matrix to adhere to the area of the skin. After a suitable duration of application, the patch is removed. The treatments and/or cleansings are repeated, depending on the needs of the user's skin. The treatments and cleansings may be scheduled so that they are suited to the needs of the skin to be treated, in terms of frequency and duration of application.

The active compounds in the cleansing mode do not have to be the same as those in treatment mode. The selecting of cleansing and/or treatment is preferably chosen, depending on the needs of the skin.

APPLICATION EXAMPLE

A patch is produced which comprises:

a) a polyethylene sheet forming the reinforcing member for the patch and having a thickness of 200 µm;

b) a polymeric matrix made in the form of a layer having an average thickness of 0.2 mm, comprising:

| | |
|---|---|
| ascorbic acid | 1.5% |
| menthol | 0.5% |
| lavender essence | 0.1% |
| lactic acid | 5% |
| polyamide (ORGASOL ®) powder | 5% |
| citric acid | 1.5% |
| allantoin | 2% |
| water-absorbent polyacrylate (AQUAKEEP ®) | 5% |
| self-adhesive acrylic polymer qsp. | 100% |

This matrix has an adhesion to dry skin of about 500 g/cm²;

c) a sheet of siliconized paper forming the detachable protective film.

Examination of the surface of the matrix in the dry state shows the presence of many raised features (formed by particles of active compounds or of water-absorbent compounds, or of agglomerates of such particles) spread out more or less uniformly over the surface of the patch and projecting from the surface of the patch to a height of about 50 microns.

In order to apply the patch to the forehead, the patch is cut, for example, into a 3 cm×8 cm rectangle.

During the cleansing mode, the detachable protective film is removed and then the patch is applied directly to the forehead for a period of about 5 minutes. During this period, the presence of the lactic acid helps to pull away the surface dead skin cells. After this period, the patch is removed and the dead skin cells remain attached to the matrix.

After a rest period of 30 minutes, the forehead is moistened with water. A second patch of the same type is then applied to the moistened forehead and left on for about 30 minutes. Afterward, the second patch is removed and a lightening of the area treated may be observed. The lightening results from the presence of ascorbic acid and citric acid. Moreover, because of the action of allantoin, the skin of the treated area becomes more flexible and feels softer. Small wrinkles on the forehead are also smoothed away.

Besides the structural arrangements set forth above, the invention could include a number of other arrangements and procedural steps. It is to be understood that both the foregoing description are exemplary, and is intended to provide further explanation of the invention as claimed.

It will be apparent to those skilled in the art that various modifications and variations can be made to the structure and methodology of the present invention without departing from the spirit or scope of the invention.

In view of the foregoing, it is intended that the present invention cover modifications and variations of this invention, provided they fall within the scope of the following claims and their equivalents.

What is claimed is:

1. A cosmetic skin treatment method, comprising:

providing a patch configured to be used in both a cleansing mode and a treatment mode, the patch including a polymeric matrix and a reinforcing member, the polymeric matrix including at least one cosmetically active compound and at least one water-absorbent compound, wherein the patch is configured to adhere to dry skin and also to adhere to skin when at least one of the patch and skin is moistened; and selecting at least one of the cleansing mode and the treatment mode;

wherein when the cleansing mode is selected, the method further comprises applying the patch to an area of dry skin so that the polymeric matrix adheres to the skin for a time sufficient to allow at least one impurity in the area of skin to become attached to the polymeric matrix and removing the patch from the area of skin while said at least one impurity is attached to the polymeric matrix; and wherein when the treatment mode is selected, the method further comprises moistening at least one of the patch and an area of skin, applying the patch to the area of skin so that the patch adheres to the area of skin, and allowing at least some of the cosmetically active compound to contact the area of skin.

2. The method according to claim 1, wherein an adhesion force between the patch and dry skin is greater than an adhesion-force between the patch and skin when at least one of the patch and skin is moistened.

3. The method according to claim 1, wherein when the treatment mode is selected, the allowing further includes allowing at least some of the cosmetically active compound to become dissolved in the moisture.

4. The method according to claim 1, wherein when the treatment mode is selected, the method further comprises removing the patch from the area of skin.

5. The method according to claim 1, wherein the reinforcing member is occlusive.

6. The method according to claim 1, wherein the reinforcing member is formed of a thermoplastic chosen from high-density and low-density polyethylenes, polypropylenes, polyvinyl chlorides, ethylene-vinyl acetate copolymers, polyurethanes and polyesters, or is made of a complex of thermoplastics chosen from polyethylene terephthalate covered with an aluminium foil.

7. The method according to claim 1, wherein the reinforcing member is non-occlusive.

8. The method according to claim 7, wherein the reinforcing member is chosen from paper, porous thermoplastics, perforated thermoplastics, woven fabrics, and nonwoven fabrics.

9. The method according to claim 8, wherein the nonwoven fabrics include perforated nonwoven fabrics.

10. The method according to claim 1, wherein the selecting includes selecting both the cleansing mode and the treatment mode, and wherein the cleansing mode is performed prior to the treatment mode.

11. The method according to claim 1, wherein the selecting includes selecting both the cleansing mode and the treatment mode, and wherein the treatment mode is performed prior to the cleansing mode.

12. The method according to claim 1, wherein the selecting includes selecting at least the treatment mode, and wherein said at least one cosmetically active compound is dispersed in said polymeric matrix in particulate form.

13. The method according to claim 1, wherein the selecting includes selecting at least the treatment mode, and wherein said at least one cosmetically active compound is chosen from emollients, moisturizers, softening agents, keratolytic agents, desquamating agents, cicatrizing agents, regenerating agents, anti-wrinkle agents, tautening agents, sunscreen agents, soothing agents, self-tanning agents, lightening agents, bleaching agents, antioxidants, free-radical scavengers, liporegulating agents, anti-acne agents, anti-ageing agents, anti-inflammatory agents, refreshing agents, vascular protecting agents, antibacterials, antifungals, and nourishing agents.

14. The method according to claim 13, wherein said emollients are chosen from volatile and non-volatile silicones, polydiorganosiloxane-polyoxyalkylene copolymers; natural and synthetic oils; fats and waxes; fatty alcohols and acids, and their esters; esters and ethers of (poly)alkylene glycols; hydrocarbons; lanolin alcohol and its derivatives; animal and plant triglycerides; and stearyl alcohol.

15. The method according to claim 14, wherein said natural and synthetic oils are chosen from mineral, plant, and animal oils.

16. The method according to claim 14, wherein said hydrocarbons are chosen from isohexadecane, petrolatum, and squalane.

17. The method according to claim 13, wherein said moisturizers are chosen from glycerol, sorbitol and its derivatives, propylene glycol, dipropylene glycol, butylene glycol, D- and DL-panthenol and derivatives thereof.

18. The method according to claim 13, wherein said softening agent is allantoin.

19. The method according to claim 13, wherein said desquamating agents are chosen from alkylated derivatives of salicylic acid, 5-(n-octanoyl)salicylic acid, alpha- and beta-hydroxycarboxylic acids, beta-ketocarboxylic acids, their salts, amides and esters.

20. The method according to claim 13, wherein said tautening agents are chosen from alpha- and beta-hydroxycarboxylic acids, beta-ketocarboxylic acids, their salts, amides and esters; salicylic acid, ascorbic acid, azelaic acid, retinol and their derivatives.

21. The method according to claim 13, wherein said sunscreen agents are chosen from UV-A filters and UV-B filters.

22. The method according to claim 13, wherein said soothing agent is alpha-bisabolol.

23. The method according to claim 13, wherein said self-tanning agents are chosen from dihydroxyacetone and derivatives of hydroxynaphthoquinone.

24. The method according to claim 13, wherein said lightening agents are chosen from citric acid, hydroquinone, kojic acid, and ascorbic acid.

25. The method according to claim 13, wherein said keratolytic agents are chosen from alpha- and beta-hydroxycarboxylic, acids, beta-ketocarboxylic acids, and the salts, amides and esters thereof.

26. The method according to claim 1, wherein said at least one cosmetically active compound is chosen from keratolytic agents, antibacterials and antibiotics.

27. The method according to claim 26, wherein said keratolytic agents are beta-hydroxy acids and alpha-hydroxy acids, the alpha-hydroxyacids being chosen from glycolic acid, lactic acid, tartaric acid, malic acid, citric acid, mandelic acid, and fruit acids.

28. The method according to claim 27, wherein said beta-hydroxy acids are chosen from salicyclic acid and its derivatives.

29. The method according to claim 28, wherein said derivatives are alkylated derivatives.

30. The method according to claim 29, wherein said alkylated derivatives are chosen from 5-(n-octanoyl) salicyclic acid and its esters.

31. The method according to claim 1, wherein said polymeric matrix further comprises kaolin powder, burnt Sienna, zeolites, polyamide particles, powder of expanded thermoplastic microspheres, and modified starch powder.

32. The method according to claim 26, wherein said antibacterials are chosen from clindamycin and erythromycin phosphate.

33. The method according to claim 26, wherein said antibiotics are chosen from tetracycline.

34. The method according to claim 1, wherein the cosmetically active compound is chosen from one of emollients, softening agents, cicatrizing agents, and astringent agents.

35. The method according to claim 34, wherein said emollients are chosen from honey and waxes.

36. The method according to claim 1, wherein the cosmetically active compound is chosen from certain mineral salts.

37. The method according to claim 36, wherein said cosmetically active compound is zinc oxide.

38. The method according to claim 34, wherein said astringent agents are chosen from tannins, aluminum, and zirconium chlorohydrates.

39. The method according to claim 1, wherein said at least one cosmetically active compound is chosen from ascorbic acid and its biologically compatible salts and esters, enzymes, tautening agents, hydoxylated polyacids, sucroses and their derivatives, urea, amino acids, oligopeptides, water-soluble plant and yeast extracts, protein hydrolystates, hyaluronic acids, mucopolysaccharides, vitamins $B_2$, $B_6$, H and PP, panthenol, folic acids, acetylsalicyclic acids, allantoin, kojic acids, and hyrodquinones.

40. The method according to claim 39, wherein said tautening agents are chosen from protein, soya powders and wheat powders.

41. The method according to claim 39, wherein said protein hydrolysates are chosen from collagen and elastin hydrolysates.

42. The method according to claim 1, wherein said at least one cosmetically active compound comprises at least one liposoluble compound chosen from D-α-tocopherol, DL-α-tocopherol, D-α-tocopherol acetate, DL-α-tocopherol acetate, ascorbyl palmitate, vitamin F and vitamin F glycerides, vitamins D, vitamin $D_2$, vitamin $D_3$, retinol, retinol esters, retinol palmitate, retinol propionate, β-carotene, D-panthenol, farnesol, farnesyl acetate; jojoba and blackcurrant oils rich in essential fatty acids; keratolytic agents; asiatic acid, madecassic acid, asiaticoside, total extract of centella asiatica, β-glycyrrhetinic acid, α-bisabolol, ceramides; phytanetriol, milk sphingomyelin, phospholipids of marine origin, rich in polyunsaturated essential fatty acids, ethoxyquin; extract of rosemary, extract of melissa, quercetin, extract of dried microalgae, and steroidal anti-inflammatory drugs.

43. The method according to claim 42, wherein said keratolytic agents are chosen from salicylic acid, its salts and its esters, 5-(n-octanoyl)salicylic acid and its esters, and alkyl esters of α-hydroxy acids.

44. The method according to claim 43, wherein said alkyl esters of α-hydroxy acids are chosen from alkyl esters of citric acid, lactic acid and glycolic acid.

45. The method according to claim 42, wherein said ceramides is 2-oleoylamino-1,3-octadecane.

46. The method according to claim 1, wherein the polymeric matrix includes at least one of acrylic and vinyl polymer.

47. The method according to claim 1, wherein the water-absorbent compound is chosen from superabsorbent crosslinked polyacrylates; polyvinyl alcohol; carboxyvinyl polymers; semi-synthetic derivatives of cellulose; starches; biogums; casein; phytocolloids; gelatin and cotton fibers.

48. The method according to claim 47, wherein said biogums are chosen from xanthan gum, guar gum, gum arabic, gum tragacanth, biosaccharides, and scleroglucans.

49. The method according to claim 47, wherein said phytocolloids are alginates.

50. The method according to claim 1, wherein a portion of the patch extends from the patch, said portion forming a grip to facilitate removal of the patch from the area of skin.

51. The method according to claim 1, wherein the patch is colored to allow a user to quantify and/or qualify said at least one impurity when the cleansing mode is selected.

52. The method according to claim 51, wherein the polymeric matrix is colored by pigment in the polymeric matrix.

53. The method according to claim 51, wherein the color of the patch is dark to contrast said at least one impurity extracted from the skin during the cleansing mode so that the at least one impurity is visible.

54. The method according to claim 1, wherein the reinforcing member is embedded in the polymeric matrix.

55. The method according to claim 1, wherein the patch further comprises a protective film configured to be peeled off before the patch is applied.

56. The method according to claim 55, wherein the protective film is impermeable to said at least one cosmetically active compound and said at least one water-absorbent compound in the polymeric matrix.

57. The method according to claim 55, wherein the protective film includes two parts superposed on a central portion of the patch.

58. The method according to claim 1, wherein the patch is shaped to fit on at least one body part chosen from a nose, at least one lip, a region between a nose and an upper lip, an outer corner of at least one eye, under at least one eye, and on the forehead.

59. The method according to claim 58, wherein at least the treatment mode is selected, and wherein the patch is applied to an area of skin in the outer corner of at least one eye to treat crow's feet.

60. The method according to claim 58, wherein at least the treatment mode is selected, and wherein the patch is applied to the forehead to treat forehead wrinkles.

61. The method according to claim 1, wherein the selecting includes alternately selecting the cleansing mode and the treatment mode.

62. The method according to claim 1, wherein the selecting includes selecting at least the cleansing mode, and wherein the polymeric matrix adheres to the skin from 5 seconds to 5 minutes.

63. The method according to claim 1, wherein the adhesion force between the skin and the dry patch is from 300 $g/cm^2$ to 800 $g/cm^2$.

64. The method according to claim 1, wherein the adhesion force between the patch and skin when at least one of the patch and skin are moistened is from 20 $g/cm^2$ to 300 $g/cm^2$.

65. The method according to claim 1, wherein the selecting includes selecting the cleansing mode at least twice and the treatment mode at least twice, and wherein the cleansing mode and the treatment mode are alternated.

66. A cleansing and treatment patch, the patch comprising:
   a reinforcing member; and
   a polymeric matrix, the polymeric matrix including at least one cosmetically active compound and at least one water-absorbent compound, the patch being configured to adhere to dry skin and also to adhere to skin when at least one of the patch and skin are moistened;
   wherein the patch is configured so that when the patch is used in a cleansing mode and the patch is applied to an area of dry skin, the patch adheres to the area for a sufficient time to allow at least one impurity in the area of skin to become attached to the polymeric matrix so that the impurity is removed from the area of skin when the patch is removed from the area of skin, and wherein the patch is configured so that when the patch is used in a treatment mode and at least one of the patch and an area of skin is moistened, at least some of the at least one cosmetically active compound contacts the area of skin.

67. The patch according to claim 66, wherein the patch is configured so that when the patch is used in the treatment mode and at least one of the patch and an area of skin is moistened, at least some of the at least one cosmetically active compound becomes dissolved in the moisture.

68. The patch according to claim 66, wherein the polymeric matrix includes at least one of particles of the water-absorbent compound, groups of the water-absorbent compound particles, particles of the cosmetically active compound, and groups of the cosmetically active compounds.

69. The patch according to claim 68, wherein the particles are arranged along at least one surface of the matrix and wherein the particles form an interface layer in a wet state.

70. The patch according to claim 69, wherein a thickness of the particles on the surface ranges from about 10 microns to about 100 microns.

71. The patch according to claim 70, wherein a thickness of the particles on the surface ranges from about 10 microns to about 70 microns.

72. The patch according to claim 66, wherein the active compound forms an interface layer between the polymeric matrix and the skin when the active compound is dissolved.

73. The patch according to claim 72, wherein the interface layer has a thickness ranging from about 50 microns to about 100 microns.

74. The method according to claim 1, wherein when the treatment mode is selected, the method further comprises absorbing at least some of the moisture with the water-absorbent compound and thereby at least partially drying the skin to provide at least some of the adhesion of the matrix to the skin.

75. The method according to claim 1, wherein the selecting includes selecting the treatment mode and wherein the patch is applied to the skin from about 5 seconds to about 5 minutes.

76. The method according to claim 1, wherein said polymeric matrix further comprises essential oils.

77. The method according to claim 76, wherein said essential oils are chosen from lavender, mint, pepper, nutmeg, clove, cedar, wheatgerm, calophyllum, cartham, coriander and fruit pip oils.

78. The method according to claim 77, wherein said fruit pip oils are chosen from grape, blackcurrant, orange and kiwi oils.

79. The patch according to claim 66, wherein the patch is configured so that an adhesion force between the patch and dry skin is greater than an adhesion force between the patch and skin when at least one of the patch and skin are moistened.

80. A cosmetic skin treatment method, comprising:

providing the patch of claim 66; and selecting at least one of the cleansing mode and the treatment mode;

wherein when the cleansing mode is selected, the method further comprises
applying the patch to an area of dry skin so that the polymeric matrix adheres to the skin for a time sufficient to allow at least one impurity in the area of skin to become attached to the polymeric matrix and
removing the patch from the area of skin while said at least one impurity is attached to the polymeric matrix; and wherein when the treatment mode is selected, the method further comprises
moistening at least one of the patch and an area of skin,
applying the patch to the area of skin so that the patch adheres to the area of skin, and
allowing at least some of the cosmetically active compound to contact the area of skin.

81. The patch according to claim 66, wherein the reinforcing member is configured to provide a coating for protecting the polymeric matrix.

* * * * *

UNITED STATES PATENT AND TRADEMARK OFFICE
CERTIFICATE OF CORRECTION

PATENT NO. : 6,419,935 B1
DATED : July 16, 2002
INVENTOR(S) : Jean-Louis H. Gueret It is certified that error appears in the above-identified patent and that said Letters Patent is hereby corrected as shown below:

<u>Title page,</u>
Item [57], ABSTRACT,
Line 11, replace "areas" with -- area --.

<u>Column 12,</u>
Line 41, after "hydroxycarboxylic", delete the comma.

<u>Column 13,</u>
Line 20, replace "hydrolystates," with -- hydrolysates, --.
Line 23, replace "hyrodquinones" with -- hydroquinones --.

Signed and Sealed this

Seventeenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,419,935 B1
DATED : July 16, 2002
INVENTOR(S) : Jean-Louis H. Gueret It is certified that error appears in the above-identified patent and that said Letters Patent is hereby corrected as shown below:

<u>Title page,</u>
Item [57], ABSTRACT,
Line 11, replace "areas" with -- area --.

<u>Column 12,</u>
Line 41, after "hydroxycarboxylic", delete the comma.

<u>Column 13,</u>
Line 20, replace "hydrolystates," with -- hydrolysates, --.
Line 23, replace "hyrodquinones" with -- hydroquinones --.
Line 54, replace "is" with -- are --.

Signed and Sealed this

Eleventh Day of November, 2003

JAMES E. ROGAN
*Director of the United States Patent and Trademark Office*